United States Patent
Spratt et al.

(10) Patent No.: US 8,985,767 B2
(45) Date of Patent: Mar. 24, 2015

(54) WAVEFRONT OPTIMIZED PROGRESSIVE LENS

(71) Applicants: Carl Zeiss Vision Inc., San Diego, CA (US); Carl Zeiss Vision International GmbH, Aalen (DE)

(72) Inventors: Ray Steven Spratt, Petaluma, CA (US); Darryl Meister, Olathe, KS (US); Timo Kratzer, Aalen (DE)

(73) Assignees: Carl Zeiss Vision International GmbH, Aalen (DE); Carl Zeiss Vision Inc., San Diego, CA (US)

( * ) Notice: Subject to any disclaimer, the term of this patent is extended or adjusted under 35 U.S.C. 154(b) by 46 days.

(21) Appl. No.: 13/722,892

(22) Filed: Dec. 20, 2012

(65) Prior Publication Data
US 2013/0107204 A1 May 2, 2013

Related U.S. Application Data (63) Continuation of application No. PCT/US2010/050988, filed on Sep. 30, 2010.

(60) Provisional application No. 61/365,033, filed on Jul. 16, 2010.

(51) Int. Cl.
G02C 7/02 (2006.01)
G02C 7/06 (2006.01)
A61B 3/00 (2006.01)

(52) U.S. Cl.
CPC . *A61B 3/00* (2013.01); *G02C 7/027* (2013.01); *G02C 7/028* (2013.01); *G02C 7/061* (2013.01); *G02C 2202/22* (2013.01)
USPC ............. 351/159.74; 351/159.06; 351/159.42

(58) Field of Classification Search
USPC .................................................. 351/159.74
See application file for complete search history.

(56) References Cited

U.S. PATENT DOCUMENTS

| | | | |
|---|---|---|---|
| 4,838,675 A | 6/1989 | Barkan et al. | |
| 4,956,682 A | 9/1990 | Ohnaka et al. | |
| 6,089,713 A | 7/2000 | Hof et al. | |
| 6,655,803 B1 * | 12/2003 | Rubinstein et al. | 351/159.74 |

(Continued)

FOREIGN PATENT DOCUMENTS

| | | |
|---|---|---|
| CN | 101297230 | 10/2008 |
| EP | 1 950 601 | 7/2008 |

(Continued)

OTHER PUBLICATIONS

Chinese Office Action, with translation thereof, for corresponding CN Appl No. 201080068080.4, dated Nov. 15, 2013.

(Continued)

*Primary Examiner* — Jordan Schwartz
(74) *Attorney, Agent, or Firm* — Fish & Richardson P.C.

(57) ABSTRACT

A method for designing a progressive lens is disclosed. The method includes obtaining a wavefront measurement of an eye, determining an initial design for the progressive lens based on the wavefront measurement, determining information about how changes in one or more higher order aberrations of the eye affect a second order correction for the aberrations of the eye based on information derived from the wavefront measurement, modifying the initial design of the progressive lens to provide a final progressive lens design, and outputting the final lens design.

28 Claims, 6 Drawing Sheets

(56) References Cited

U.S. PATENT DOCUMENTS

| | | | |
|---|---|---|---|
| 7,029,119 | B2 | 4/2006 | Youssefi et al. |
| 7,063,421 | B2 | 6/2006 | Wehner et al. |
| 7,077,522 | B2 | 7/2006 | Williams |
| 7,334,245 | B2 | 2/2008 | Yasukawa et al. |
| 7,731,359 | B2 | 6/2010 | Guilloux et al. |
| 7,744,217 | B2 | 6/2010 | Cabeza et al. |
| 2003/0090623 | A1 | 5/2003 | Rubinstein et al. |
| 2005/0083482 | A1 | 4/2005 | Miller et al. |
| 2005/0206842 | A1 | 9/2005 | Wehner et al. |
| 2006/0119791 | A1 | 6/2006 | Dreher |
| 2007/0035696 | A1 | 2/2007 | Altheimer et al. |
| 2007/0097318 | A1 | 5/2007 | Chehab et al. |
| 2007/0115432 | A1* | 5/2007 | Thibos .......................... 351/246 |
| 2007/0279586 | A1 | 12/2007 | Jethmalani et al. |
| 2009/0015787 | A1 | 1/2009 | Guillen et al. |
| 2010/0079722 | A1 | 4/2010 | Guilloux et al. |
| 2010/0145489 | A1 | 6/2010 | Esser et al. |
| 2010/0198515 | A1 | 8/2010 | Becken et al. |
| 2011/0255052 | A1* | 10/2011 | Meister et al. ................ 351/176 |

FOREIGN PATENT DOCUMENTS

| | | |
|---|---|---|
| WO | WO 01/92948 | 12/2001 |
| WO | WO 03/048841 | 6/2003 |
| WO | WO 2004/038488 | 5/2004 |
| WO | WO 2005/036238 | 4/2005 |
| WO | WO 2007/062784 | 7/2007 |
| WO | WO 2008/089999 | 7/2008 |

OTHER PUBLICATIONS

English translation of Chinese Office Action for corresponding CN Appl No. 201080068080.4, dated Nov. 15, 2013.

Gross et al., "Handbook of Optical Systems", vol. 3: Aberration Theory and Correction of Optical Systems, WILEY-VCH Publishing, Weinheim, chapter 29, pp. 1-69, 2007.

Gross et al., "Handbook of Optical Systems", vol. 5: Metrology of Optical Components and Systems, WILEY-VCH Publishing, Weinheim, section 47.8, pp. 283-297, 2007.

Dai et al., "Wavefront propagation from one plane to another with the use of Zernike polynomials and Taylor monomials," *Applied Optics*, Optical Society of America, vol. 48, Issue 3, pp. 477-488, 2009.

International Preliminary Report on patentability from the counterpart PCT Application No. PCT/EP2010/050988, dated Jan. 22, 2013.

International Search Report and a Written Opinion from the counterpart PCT Application No. PCT/EP2010/050988, dated Mar. 23, 2011.

Loos et al., "A variational approach to progressive lens design," Computer Aided Design, vol. 30, No. 8, pp. 595-602, 1998.

J. Schwiegerling, excerpt from Field Guide to Visual and Ophthalmic Optics, SPIE Press, Bellingham, WA (2004). http://spie.org/x32355.xml, retrieved Sep. 2, 2014.

Chinese Office Action, with translation thereof, for CN Appl No. 201080068080.4, dated Sep. 22, 2014.

\* cited by examiner

WAVEFRONT OPTIMIZED PROGRESSIVE LENS

CROSS-REFERENCE TO RELATED APPLICATIONS

This application is a continuation of, and claims benefit under 35 USC 120 to, international application PCT/US2010/050988, filed Sep. 30, 2010, which claims benefit under 35 USC 119(e) of U.S. Ser. No. 61/365,033, filed Jul. 16, 2010. Both applications are incorporated by reference herein in their entirety.

TECHNICAL FIELD

This invention relates to opthalmic lenses, and more particularly to progressive lenses and methods for designing such lenses.

BACKGROUND

Wavefront aberrations are the result of differences in optical path length between an ideal wavefront that would result in a perfect focus through an optical system, e.g., an opthalmic lens and the eye, and the aberrated wavefront that is produced by the actual optical system. Wavefront aberrations are often categorized by their radial order, which indicates the dependence of the aberration on pupil size. The optical components of the human eye suffer from both "low-order" and "high-order" wavefront aberrations. The low-order aberrations of interest to the correction of vision are actually a subset of the low-order aberrations, referred to as the "second-order" wavefront aberrations. Second-order aberrations vary as a function of the square of the distance from the center of the pupil or aperture. These wavefront aberrations are typically corrected with an eyeglass prescription that includes a spherical power component, a cylindrical power component and an axis component that describes the orientation of the cylindrical power.

High-order aberrations (HOAs) represent wavefront aberrations that vary as a cubic or higher order function of the distance from the center of the pupil or aperture. The HOAs of the eye include aberrations such as, for example, coma, trefoil and spherical aberrations. Although these aberrations are often smaller in magnitude than the low-order aberrations, HOAs of the eye can also degrade vision quality and limit visual performance.

It is possible to improve vision quality by correcting the HOAs of the eye in addition to the low-order aberrations. The eye examination and lens design procedures for conventional eyeglass prescriptions (Rxs), however, typically only yields a correction that minimizes the low-order aberration of the eye. This is generally true for single-vision lenses, bifocal lenses, and progressive lenses.

Progressive lenses, which are also referred to as progressive addition lenses (PALs), progressive power lenses, graduated prescription lenses, and varifocal or multifocal lenses, are corrective lenses used in eyeglasses to correct presbyopia and other disorders of accommodation. They are characterized by a gradient of increasing lens power, added to the wearer's correction for the other refractive errors. Typically, the gradient starts at the wearer's distance prescription, in the upper portion of the lens and reaches a maximum addition power, or the full reading addition, in the lower portion of the lens. The final addition power is between 0.75 to 3.00 diopters for most wearers. The addition value prescribed generally depends on the level of presbyopia of the patient and is often closely related to age and to a lesser extent, existing prescription.

Figure 1:
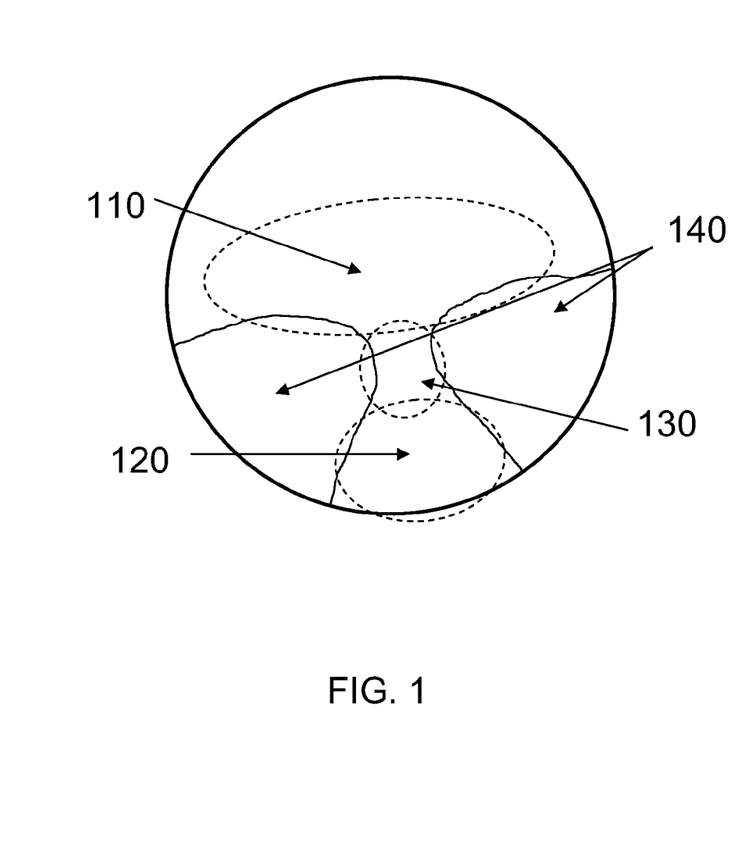
FIG. 1 is a schematic of a system for making a progressive addition lens (PAL)

Referring to FIG. 1, general-purpose PALs typically belong to a class of surfaces that include four specific structural features: a distance zone 110, a near zone 120, a progressive corridor 130 and a blending region 140. Distance zone 110 is a stabilized region in the upper portion of the lens that provides the specified distance prescription. Near zone 120 provides a stabilized region in the lower portion of the lens that provides a specified add power for reading. Progressive corridor 130 connects distance zone 110 with near zone 120 and provides intermediate or mid-range vision. Blending regions 140 are peripheral regions of the lens and contain surface astigmatism, which produce blur and distortion and offer only minimal visual utility.

SUMMARY

Conventional progressive lens designs are typically based on the assumption the wearer's eye are free of high-order aberrations (HOAs). However, progressive lenses produce significant third order aberrations such as coma and trefoil within the progressive corridor and at the boundaries between the central viewing zones of the lens and the peripheral regions. Both low-order and HOAs are unavoidable in certain areas of progressive additional lenses due to the use of blending regions that provide a smooth change in addition power without visible lines of demarcation.

It is possible to take into account of HOAs in PAL design by evaluating a cost function in which a detailed description of the eye (including the HOAs of the eye) are combined with a detailed description of the lens surface (including the HOAs of the lens) at multiple discrete locations over the lens surface. However, such cost functions can be extremely expensive, computationally.

The inventors have realized that a cost function in PAL optimization can remain essentially unchanged and is not directly coupled to the detailed HOA distribution of the eye. Instead a target vergence distribution for the eye can be altered using only the aberration in the lens and scalar coefficients derived from the aberration of the eye.

This process can allow one to use current, well-tested custom progressive lens design tools (such as disclosed in U.S. Pat. Nos. 4,838,675; 6,956,682; 7,334,245, and 7,731,359, for example) to make wave-front optimized lenses (i.e., lenses that account for HOAs of the eye). The method uses the original cost function, and only alters the target vergence distribution. There is no need for direct combining of the HOAs of the eye with the HOAs of the lens.

Generally, designing the progressive lenses involves combining methods of obtaining an optimum Rx, second order correction only, based on the aberrations experienced by the eye and optimizing a cost function based on spatially varying weights and a spatially varying target vergence distribution. In general, the main variables in this approach are how many HOAs to consider and how many coefficients (e.g., Taylor series coefficients) to calculate and apply for the various HOAs. Generally, a linear Taylor series correction term for coma in the lens is included. Including higher order HOAs of the lens, and higher power Taylor series terms may also be beneficial.

While a Taylor series approach may be especially efficient, other ways of modifying the target vergence other than scaling the HOAs of the lens by Taylor coefficients derived from the eye may be used. For example, one could calculate coefficients coupling the HOAs to the second order aberrations using least squares. In some embodiments, a Fourier series expansion or an expansion using Chebychev polynomials can be used.

Various aspects of the invention are summarized as follows.

In general, in a first aspect, the invention features a method for designing a progressive lens, the method including obtaining a wavefront measurement of an eye, the wavefront measurement including information about second order aberrations of the eye and about higher order aberrations of the eye; determining an initial design for the progressive lens based on the wavefront measurement, the initial design including, for one or more points on the lens, information about second order aberrations of the progressive lens and higher order aberrations of the progressive lens, the initial design providing a target correction for the eye in the absence of the higher order aberrations of the eye; determining information about how changes in one or more higher order aberrations of the eye affect a second order correction for the aberrations of the eye based on information derived from the wavefront measurement; modifying the initial design of the progressive lens to provide a final progressive lens design, wherein the modification accounts for an expected variation of the correction from the target correction due to one or more higher order aberrations of the initial progressive lens design and the information about how changes in one or more higher order aberrations of the eye affect the second order correction for the aberrations of the eye; and outputting the final lens design. The method of claim 1, wherein the initial design of the progressive lens is based on the second order correction for the aberrations of the eye determined from the wavefront measurement.

Implementations of the method can include one or more of the following features. For example, the initial design can be a stock progressive lens design corresponding to the second order correction for the aberrations of the eye.

Determining information about how one or more higher order aberrations of the eye affect the second order correction for the aberrations of the eye can include determining a power series expansion of the aberrations of the eye. The power series expansion can be a Taylor series expansion. The power series expansion can include a linear term for at least one third order aberration of the eye. The power series expansion can include a linear term for coma.

Determining information about how changes in one or more higher order aberrations of the eye affect the second order correction for the aberrations of the eye can include determining a scalar quantity coupling each of the one or more of the higher order aberrations of the eye to each of the second order corrections.

The higher order aberrations of the eye can include third order aberrations and/or fourth order aberrations.

Modifying the initial design of the progressive lens to provide a final progressive lens design can include finding a vergence of the initial design, modifying that vergence into a new target vergence, and optimizing a lens design to correspond to the new target vergence, the optimized lens design being the final progressive lens design.

Modifying the initial design of the progressive lens to provide a final progressive lens design can include pre-compensating second order correction values at multiple locations on the initial design based on the one or more higher order aberrations of the initial progressive lens design at each location and the information about how changes in one or more higher order aberrations of the eye affect the second order correction for the aberrations of the eye. Modifying the initial lens design further can include optimizing a lens design having the pre-compensated second order correction values. The optimizing can be performed using a cost function. Optimizing can be performed by determining a least squares sum of the cost function.

The method can include making a measurement of the eye to obtain the wavefront measurement.

The method can include making a progressive lens element based on the final progressive lens design.

In another aspect, the invention features a progressive lens element produced according to a final progressive lens design determined using the method above.

In general, in a further aspect, the invention features a non-transitory computer readable storage medium encoded with executable instructions including instructions operable on a processor to determine an initial design for the progressive lens based a wavefront measurement of the eye, the initial design including, for one or more points on the lens, information about second order aberrations of the progressive lens and higher order aberrations of the progressive lens, the initial design providing a target correction for the eye in the absence of higher order aberrations of the eye; instructions operable on a processor to determine information about how one or more higher order aberrations of the eye affect a second order correction for the aberrations of the eye based on information derived from a wavefront measurement of the eye; instructions operable on a processor to modify the initial design of the progressive lens to provide a final progressive lens design, wherein the modification accounts for an expected variation of the correction from the target correction due to one or more higher order aberrations of the initial progressive lens design and the information about how one or more higher order aberrations of the eye affect the second order correction for the aberrations of the eye; and instructions operable on a processor to output the final progressive lens design.

Embodiments of the non-transitory computer readable storage medium can include instructions corresponding to features of other aspects.

In general, in another aspect, the invention features a system for determining a progressive lens design for a patient's eye, the system including a processor, and the non-transitory computer readable storage medium encoded with executable instructions of the foregoing aspect, wherein during operation the processor executes the instructions stored on the storage medium and the system outputs the final progressive lens design.

In general, in a further aspect, the invention features a method for designing a progressive lens, the method including determining an initial design for the progressive lens based on a prescription for an eye, the initial design providing a target correction for the eye in the absence of third or higher order aberrations of the eye; determining how the prescription for the eye changes due to contributions from third or higher order aberrations of the eye; determining information about one or more third or higher order aberrations of the lens for multiple locations on the initial lens design; modifying the initial design of the progressive lens to provide a final progressive lens design, wherein the modification comprises pre-compensating the initial lens design at the multiple locations to account for an expected variation of the correction for the eye from the target correction due to the one or more third or higher order aberrations of the initial progressive lens design and how the prescription for the eye changes due to contributions from third or higher order aberrations of the eye; and outputting the final lens design.

Implementations of the method can include one or more feature of other aspects. In general, in a further aspect, the invention features a non-transitory computer readable storage medium encoded with executable instructions including instructions operable on a processor to determine an initial design for the progressive lens based on a prescription for an eye, the initial design providing a target correction for the eye in the absence of third or higher order aberrations of the eye; instructions operable on a processor to determine how the prescription for the eye changes due to contributions from third or higher order aberrations of the eye; instructions operable on a processor to determine information about one or more third or higher order aberrations of the lens for multiple locations on the initial lens design; instructions operable on a processor to modify the initial design of the progressive lens to provide a final progressive lens design, wherein the modification comprises pre-compensating the initial lens design at the multiple locations to account for an expected variation of the correction for the eye from the target correction due to the one or more third or higher order aberrations of the initial progressive lens design and how the prescription for the eye changes due to contributions from third or higher order aberrations of the eye; and instructions operable on a processor to output the final lens design.

Embodiments of the non-transitory computer readable storage medium can include instructions corresponding to features of other aspects.

In general, in another aspect, the invention features a system for determining a progressive lens design for a patient's eye, the system including a processor, and the non-transitory computer readable storage medium encoded with executable instructions of the foregoing aspect, wherein during operation the processor executes the instructions stored on the storage medium and the system outputs the final progressive lens design.

The details of one or more embodiments are set forth in the accompanying drawings and the description below. Other features and advantages will be apparent from the description and drawings, and from the claims.

DESCRIPTION OF DRAWINGS

FIGS. 6A and 6B are contour plots showing perceived and designed astigmatism distributions for another example. FIG. 6A shows the uncompensated distributions, while FIG. 6B shows the distributions when compensated for certain higher order aberrations. Like reference symbols in the various drawings indicate like elements.

DETAILED DESCRIPTION

In general, there are numerous approaches to defining mathematically a PAL surface. Depending upon the mathematical functions used by the lens designer to create the initial surface, the fundamental design parameters described above may be directly defined in the equations or arrived at experimentally by adjusting related parameters. If these functions are sophisticated enough to produce a sufficiently adequate and well-behaved progressive lens surface, the surface may be suitable for use without any significant refinements.

However, this "starting" surface (or surfaces) is typically optimized to minimize the difference between the optical performance of the lens and a target optical performance. This is usually done numerically using lens design software that attempts to find a physical surface that satisfies the ideal optical performance requirements of the lens design as closely as possible. Essentially, the software minimizes the differences between an actual parameter value characterizing the lens (e.g., a surface shape or the optical performance) and a theoretical target value for the parameter.

Conventional PALs designed this way ignore the effects of high-order aberrations (HOAs) of both the eye and the lens itself. As a result, the HOAs of the wearer's eye and of the lens cause optical correction the lens provides to the wearer to differ from the correction intended by the lens designer. In other words, the actual vergence distribution for the wearer of the progressive lens to differ from a target vergence distribution (i.e., the vergence the lens designer intends to provide). Here, the "vergence distribution" of a PAL refers to shape (e.g., the local curvature) of a wavefront transmitted by the PAL and provides a measure of the focusing effects of the lens. Such variations from the target vergence distribution can result, for example, in changes in the apparent size, location and symmetry of the clear zones of the lens, and/or increase peripheral distortion. Furthermore, in general, HOAs of the eye vary on an individual by individual basis. As a result, their effects should be considered for each individual, for each order of the PAL. The methods disclosed herein account for HOAs in a way that can reduce deviations of the actual vergence distribution provided by a PAL from the target vergence distribution intended by the lens designer.

Figure 2A:
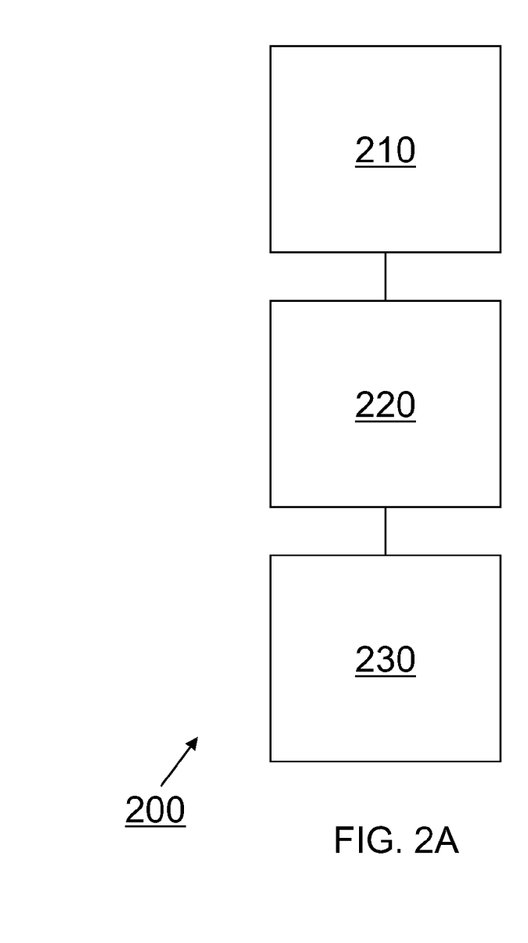
FIG. 2A is schematic of an embodiment of a system used for designing and manufacturing a PAL

Referring to FIG. 2A, a system 200 used in the design and manufacture of a PAL includes a measuring device 210, a data processing unit 120, and a production unit 230. Measuring device 210 is used to determine a wavefront aberration of an eye (or eyes) for the wearer of the PAL. In general, a variety of measuring devices can be used, such as a wavefront sensor (e.g., aberrometer). For example, a Shack-Hartmann wavefront sensor can be used. Wavefront sensors are available commercially from Abbott Medical Optics (Santa Ana, Calif.), Carl Zeiss Meditec (Dublin, Calif.), and Alcon (Fort Worth, Tex.), for example.

Data processing unit 220 is arranged to receive information about the wavefront aberration of the eye from measuring device 210 and to process this information to provide a design for the PAL. Exemplary algorithms used by data processing unit 220 are described below. Generally, a variety of different data processing units can be used. Generally, such units include one or more electronic processors in communication with a non-volatile computer readable medium storing instructions for carrying out the algorithm. Data processing unit can be a computer, either standalone or networked. In some embodiments, data processing unit 220 and measuring device 210 are part of the same system, and the electronic processor(s) of the data processing unit are used to both analyze the wavefront information acquired using the measuring device to produce information about the aberrations of the eye, and to process that information to provide the PAL design.

The lens design produced using data processing unit 220 is delivered to production unit 230, which produces the PAL based on the design. Production unit 230 can be a conventional unit (e.g., a commercially-available unit used to produce conventional PALs). In some embodiments, measuring device 210, data processing unit 220, and production unit 230 are all part of a single integrated product, that can be installed in a single location (e.g., an ophthalmic professional's office or lab). In certain embodiments, measuring device 210, data processing unit 120, and production unit 230 are all different products, in communication with each other via a communications network (e.g., the internet).

Figure 2B:
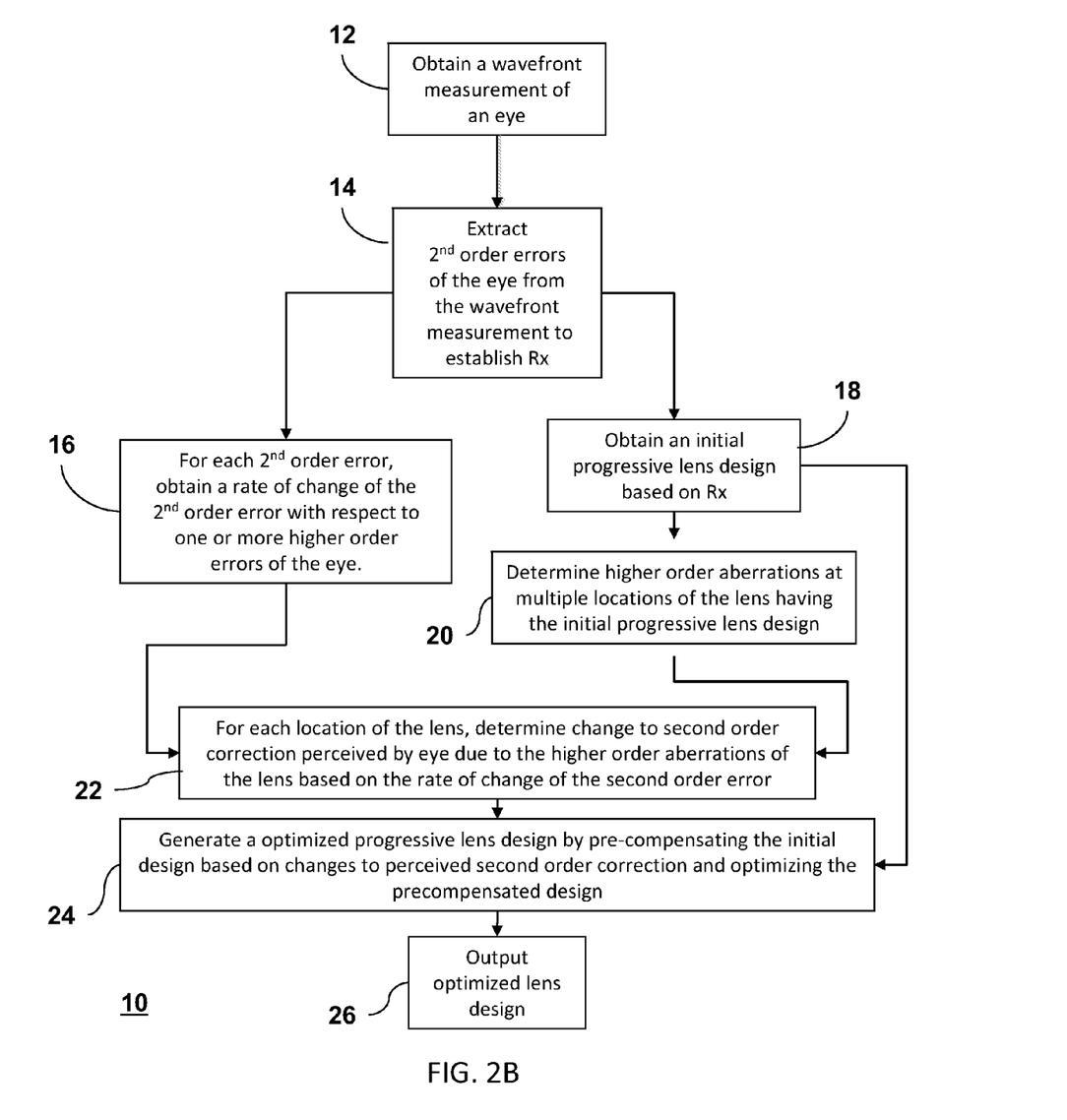
FIG. 2B is a flow chart showing a method for designing a PAL.

FIG. 2B shows a flow chart 10 of an algorithm for PAL design. Designs prepared using this algorithm account for interactions between HOAs of the eye and HOAs of the lens to reduce variations from the target vergence that would otherwise occur if HOAs were unaccounted for.

The first step is to obtain information about wavefront aberrations of the eye(s) for which the lenses are being designed (step 12). This information can be in the form of Zernike coefficients, for example. The expansion of the Zernike polynomials can, for example, be derived from Gross et al., "Handbook of Optical Systems", Vol. 1 to 6, WILEY-VCH Publishing, Weinheim, 2007, ISBN: 978-3-527-40382-0". This information includes both the second order aberrations of the eye and HOAs of the eye. While a Zernike expansion may have certain advantages (e.g., using few coefficients to convey information over a circular aperture), in general, HOAs can be supplied in a variety of forms, such as other two dimension functions; a rectangular grid of values, a Fourier expansion, etc.

In step 14, information about second order errors and HOAs of the eye are extracted from the wavefront measurement data to provide a prescription ("Rx") for the eye. The Rx corresponds to a second order correction for the aberrations of the eye for single vision lenses, commonly provided as a value for spherical or mean power ("MP"), cylinder ("cyl"), and cylinder axis, or as MP, $J_0$ and $J_{45}$ where $J_0$ and $J_{45}$ are the Jackson cross cylinder components of the correction. Conventional wavefront refraction methods can be used to determine the Rx for the eye based on the wavefront measurement data.

Typically, information about wavefront aberrations of the eye is determined for the pupil plane of the eye. However, in embodiments, the aberrated wavefront can be propagated (mathematically) from the pupil plane to another plane. For example the aberrated wavefront can be propagated to a plane for which the PAL will be optimized, such as the back vertex plane of the PAL. This propagation can be performed prior to extraction the information about different order aberrations determined in step 14. Conventional methods of wavefront error propagation can be used. For example, in some embodiments, wavefront propagation from one plane to another with the use of Zernike polynomials and Taylor monomials according to Guang-ming Dai et al., *Applied Optics*, Vol. 48, Issue 3, pp. 477-488 (2009), can be used.

In step 16, the method determines scalar coefficients that couple HOAs of the eye to the second order aberrations extracted in step 14. To do this, the effect of small changes in one or more HOAs of the eye to the second order correction established for the eye is calculated. This is explained for third order aberrations below, but, in general, the approach is applicable to aberrations of higher order as well.

For a general first order Taylor series expansion of an eyeglass prescription accounting for second and third order aberrations, there are twelve expansion coefficients; one for each coupling between the four third order aberrations with each of the three second order corrections (e.g., $J_0$ and $J_{45}$ for the cyl and MP for the mean power). The change in the $J_0$ component of the astigmatism correction, for example, $\Delta J_0$, is given by $$\Delta J_0 = \alpha_3^{-3}\Delta Z_3^{-3} + \alpha_3^{-1}\Delta Z_3^{-1} + \alpha_3^{1}\Delta Z_3^{1} + \alpha_3^{3}\Delta Z_3^{3},$$

where the $\alpha$ parameters are calculated from derivatives of the aberrations of the eye obtained from the wavefront measurement, $Z_3^{-1}$ and $Z_3^{1}$ are the Zernike coefficients for the coma, and $Z_3^{-3}$ and $Z_3^{3}$ are the coefficients for the trefoil. For example, $$\alpha_3^{-3} = \partial J_0 / \partial Z_3^{-3}, \text{ etc.}$$

In practice the derivatives, and therefore the $\alpha$ parameters, can be estimated by re-calculating the Rx components (i.e., MP, $J_0$, and $J_{45}$) for small changes in the Zernike coefficient. For example, $$\alpha_3^{-3} \approx (J_0(Z_3^{-3} = \text{eye} + \epsilon) - J_0(Z_3^{-3} = \text{eye}))/\epsilon,$$

where $J_0(Z_3^{-3} = \text{eye})$ is the original cyl component of the Rx of the eye, and $J_0(Z_3^{-3} = \text{eye} + \epsilon)$ is the correction component re-calculated with the original coefficient of $Z_3^{-3}$ replaced by $Z_3^{-3} + \epsilon$, where $\epsilon$ is small (i.e., such that $\epsilon^2$ is negligile).

Similarly for the other second order correction components;

$$\Delta J_{45} = \beta_3^{-3}\Delta Z_3^{-3} + \beta_3^{-1}\Delta Z_3^{-1} + \beta_3^{1}\Delta Z_3^{1} + \beta_3^{3}\Delta Z_3^{3}, \text{ and}$$

$$\Delta MP = \gamma_3^{-3}\Delta Z_3^{-3} + \gamma_3^{-1}\Delta Z_3^{-1} + \gamma_3^{1}\Delta Z_3^{1} + \gamma_3^{3}\Delta Z_3^{3},$$

where $$\beta_3^{-3} \approx (J_{45}(Z_3^{-3} = \text{eye} + \epsilon) - J_{45}(Z_3^{-3} = \text{eye}))/\epsilon, \text{ etc. and}$$

$$\gamma_3^{-3} \approx (MP(Z_3^{-3} = \text{eye} + \epsilon) - MP(Z_3^{-3} = \text{eye}))/\epsilon, \text{ etc.}$$

The result of the above is a simple model for how small contributions from HOAs influence the Rx for the eye.

In step 18, an initial PAL design is computed from the Rx. This design accounts only for the second order aberrations of the eye. The initial PAL design corresponds to a conventional PAL design and may correspond to a stock design (e.g., a catalogue design that provides the closest match to the desired vergence distribution) or may be further optimized to provide a vergence distribution that matches the target vergence distribution more closely than a stock lens design. Methods of lens design optimization are described in detail below.

Once the initial design is established, HOAs of the lens are determined in step 20. This can be done, for example, using ray-tracing techniques to establish the form of a wavefront transmitted by the lens at multiple locations across the lens surface. Typically, this involves establishing a grid of locations on the lens surface at which wavefront information is to be determined and tracing rays through the lens at those points. During a typical ray tracing procedure, a data processing unit determines the refraction of light through the PAL element by tracing a quantity of rays from a specified object point, sufficient to characterize the wavefront aberrations of the lens at each of the grid locations up to the chosen order. Ideally, these rays should all converge at the ideal focal plane of the eye associated with the object distance, although this may not be mathematically possible at all points across the lens aperture. Commercially-available optical modeling software can be used to perform the ray tracing. Examples of such programs include Code V (from Optical Research Associates, Inc. of Pasadena, Calif.) or Zemax (from Zemax Development Corporation of Bellevue, Wash.).

In step 22, the method determines changes to the second order correction perceived by the eye due to the HOAs of the lens calculated in step 20. This step involves evaluating, for each grid point on the lens, a difference between the target correction the lens designer wishes to provide the patient, and the actual correction provided by the lens accounting for how the HOAs of the lens change the second order correction provided to the eye based on the scalar coefficients established in step 16.

To use a simple example, the designer may wish to provide a MP value of 1.0 diopter at a particular location of the lens. However, due to the HOAs of the lens design established in step 18, the actual MP experienced by the wearer is 1.5 diopters, not 1.0 diopters. In step 22, the method calculates the difference between the experienced MP and the desired MP based on the coupling coefficients between MP and the HOAs under consideration that were established in step 16, and based on the magnitude of the HOAs established in step 20.

In step 24, the method pre-compensates the initial lens design based on changes to the perceived second order correction established in step 22. This involves reassigning second order correction values (e.g., for MP, $J_0$, $J_{45}$) so that the correction experienced by the wearer matches the target correction. Returning to the simple example presented above, this would involve reassigning an MP value at the particular location of the lens to a new values (e.g., 0.5 diopters) so that the experienced MP is 1.0 diopter.

The amount by which each second order correction term is adjusted can be established in a single step. For example, the adjustment may be established simply as the difference between the actual value and the desired value for each second order correction term.

Considering $J_0$, the change $\Delta J_0$ due to HOAs of the lens influences the original design distribution $J_0^{design}$, modifying the overall $J_0^{full}$ perceived by the wearer of the lens:

$$J_0^{full} = J_0^{design} + \Delta J_0$$

$\Delta J_0$ is a function of third (and higher) order errors and is fully characterized in step 22. One feature of the method is to use scalar coefficients (i.e., the derivatives $\alpha$, $\beta$, $\gamma$ parameters) derived from the HOAs of the eye to scale/weight the HOAs of the lens. In this way, the method obviates the need to directly combine the HOAs of the eye with the HOAs of the lens. This feature of the method stems from the realization that the cost function in progressive lens optimization remains unchanged and is not directly coupled to the detailed aberrations distribution of the eye.

Once the adjustments have been established for each location of the lens, a pre-compensated lens target design can be determined by applying the adjustments to the initial design vergences at each location. The method then generates a final PAL design by optimizing the pre-compensated target design. Optimization involves using a cost function to minimize the differences between actual vergence distribution and the target vergence distribution across the entire lens aperture. A typical optimization process seeks to achieve the desired distribution of optical powers as closely as possible by manipulating one or more continuously smooth surfaces of a PAL element. At multiple points across the lens aperture, differences in optical performance between the modeled PAL element and the target distribution are assessed using computer ray tracing, for example, for an assumed position of wear, which represents the position of the fitted lens on the wearer.

In some embodiments, the cost function is applied using a finite element method, which uses mathematical functions to model surfaces and to find solutions that minimize the cost function. An initial starting surface, corresponding to the initial PAL design, is specified and then modeled mathematically using the finite element method. This involves "discretizing" the computational area of the lens surface by breaking regions of the surface up into elements (e.g., square elements) across a reference grid, or mesh. Each intersection between these square elements represents a position on the lens surface, and is referred to as a node. Each node contains an array of mathematical quantities that can characterize the surface at that point, including its local curvatures. These nodes are mathematically connected using basis functions, such as splines.

In regions on the surface where optical performance is more critical, or changing more rapidly, the mesh can be subdivided as needed into smaller elements with additional nodes to allow tighter control of the surface in those regions. The surface characteristics at these nodes are smoothly connected by mathematical spline functions, which ensure that the surface maintains a continuous 2nd derivative between these points.

A target distribution of optical quantities, representing the ideal distribution of quantities such as mean power and astigmatism, is first determined for each node and its corresponding point on the lens surface. Generally, a smooth surface cannot achieve this target distribution—at least for every point. Finite element method seeks to minimize the difference between the desired optical performance at any point on the surface and the actual optical performance possible with a continuously smooth surface. This is accomplished by minimizing the cost function at each node, which are typically equations of the form:

$$M = \sum_i W_i (A_i - T_i)^2$$

where M is the value of the cost function to minimize at a given node location, indexed by i, W is the weighting—or importance factor—of the parameter value, A is the actual value of the parameter, and T is the target value at that point. Cost functions are used to find a "least squares" solution. Common parameters to minimize may include mean power errors, astigmatism, gradients of power, and so on.

The weightings for these quantities can vary as a function of the node location, allowing different regions of the lens surface to emphasize different performance attributes (e.g., blur in the central viewing zones and image swim in the periphery). The individual nodes, or even collections of nodes, can be weighted, as well. Some regions of the lens must maintain exact optical specifications. The central viewing zones, for instance, are more heavily weighted so that the analysis achieves the desired target performance in these regions—at the expense of the peripheral regions, if necessary.

The goal of finite element method is to minimize the total sum of all cost functions across the entire mesh. The actual surface is repeatedly (e.g., iteratively) manipulated by the program in order to reduce the sum of the entire range of cost functions across all nodes. These iterations eventually result in a real surface that comes as close as possible to producing the target optical distribution. Essentially, the process seeks to find an actual progressive surface that provides the desired optics in the central viewing zones, while minimizing optical errors elsewhere as much as possible.

The parameters for which the lens is optimized may be calculated directly from surface characteristics, such as the principal surface powers, or they may be derived after first ray tracing a lens with the intended surface characteristics. Ray tracing is the process of modeling the theoretical optical performance of the lens as perceived by the wearer with the lens in its intended position of wear—including vertex distance and pantoscopic tilt—by calculating the refraction of light rays passing through the lens from various object points.

The optimized PAL design is output by the data processing unit, e.g., to the production unit, in step 26, where a PAL corresponding to the optimized design is manufactured.

Figure 3A:
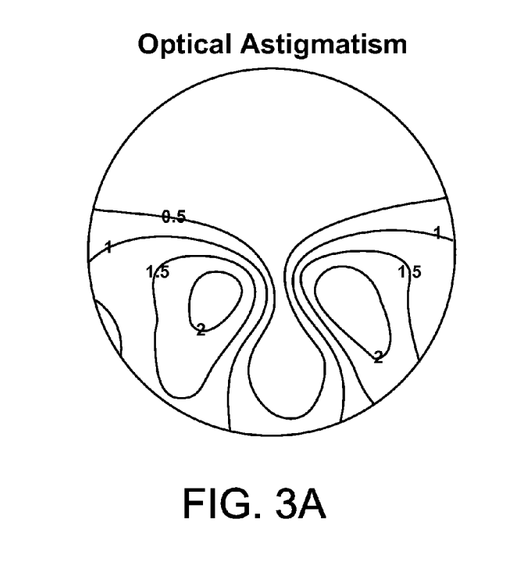
FIG. 3A is a contour plot of an exemplary target astigmatism distribution for a PAL.

This method is further explained by way of the following example. FIG. 3A shows an example of an astigmatism distribution of a PAL element used to correct second order astigmatic vergence errors. The circle represents the lens aperture and contours are shown for values of cyl in 0.5 diopter steps. In this example, this astigmatism distribution corresponds to the astigmatism for an initial PAL design generated in step 18 of method 10 described above.

However, a wearer of a lens having the astigmatism distribution shown in FIG. 3A would only perceive that exact astigmatism distribution if the wearer's eye does not have HOAs. Otherwise, HOAs of the eye interact with the HOAs of the lens to shift the "effective" astigmatism (and other Rx parameter values) in a complicated, spatially-varying way.

Figure 4A:
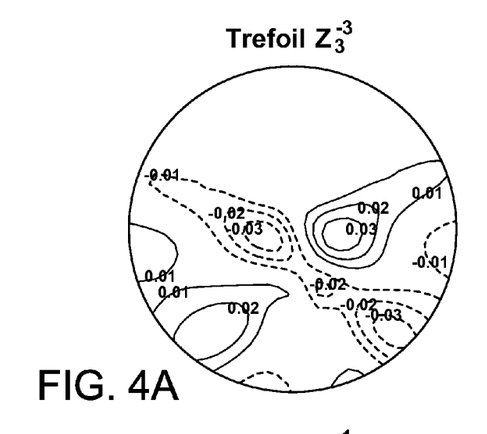
FIGS. 4A-4D are contour plots of third order aberrations for a PAL having the astigmatism distribution shown in FIG. 3A.
Figure 4B:
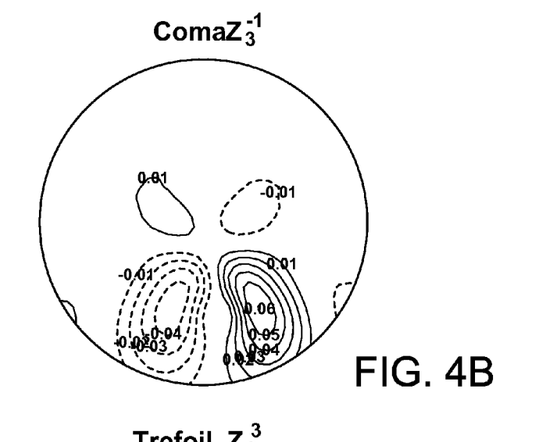
Figure 4C:
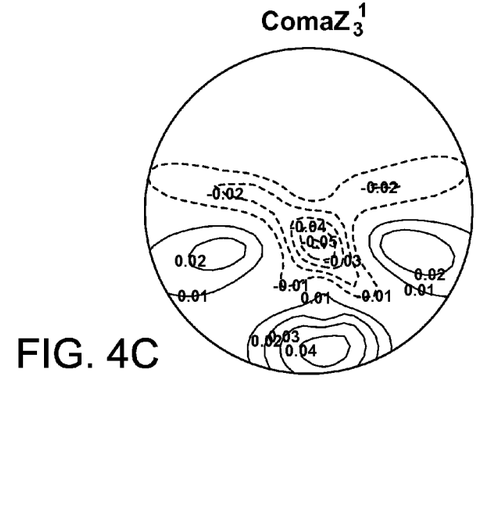
Figure 4D:
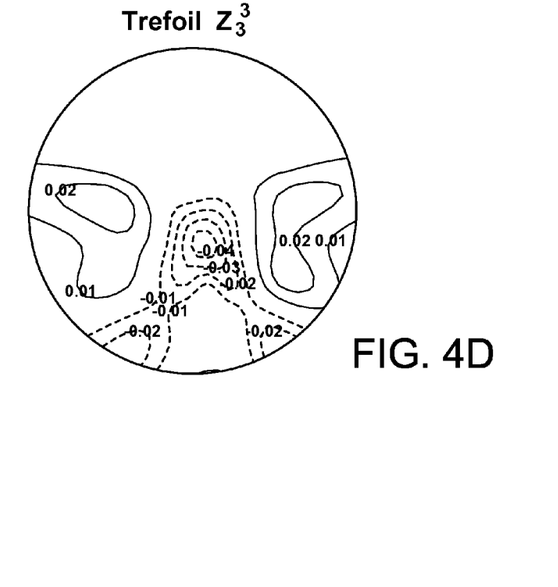

FIGS. 4A-4D show the third order aberrations of a PAL having the astigmatism distribution shown in FIG. 3A, assuming a 4 mm pupil. Specifically, FIGS. 4A and 4D shows distributions for trefoil ($Z_3^{-3}$ and $Z_3^{3}$, respectively), and FIGS. 4B and 4C show distributions for coma ($Z_3^{-1}$ and $Z_3^{1}$, respectively). For this example, it is assumed that the fourth order aberrations are small and can be ignored.

Figure 3B:
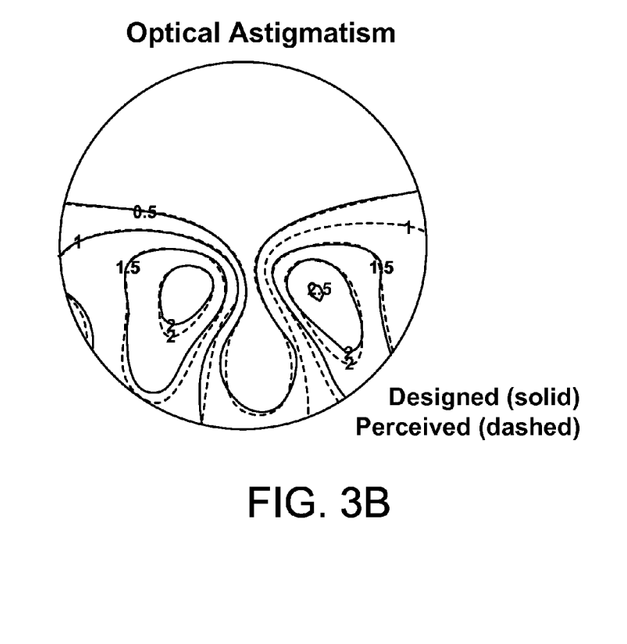
FIG. 3B is a contour plot of the target astigmatism distribution shown in FIG. 3A along the distribution perceived by a wearer when accounting for certain higher order aberrations.

For this example, assume that the only non-zero coefficient of the individual HOAs of the wearers eye from the four each $\alpha$, $\beta$, and $\gamma$ coefficients described above is $\alpha_3^{-1}=-5$. Then perceived astigmatism for the wearer would be the astigmatism of the lens minus the wearers now variable Rx. Under these circumstances, the change in the $J_0(\rho,\theta)$ component of the Rx is given by $$\Delta J_0(\rho,\theta) = -5Z_3^{-1}(\rho,\theta)$$

where $Z_3^{-1}(\rho,\theta)$ is the coma $Z_3^{-1}$ distribution of the lens shown in FIG. 4B. The net astigmatism perceived by this wearer for this lens is shown by the contour plot in FIG. 3B, plotted with the originally designed astigmatism. As is evident from this plot, the effect of the $\alpha_3^{-1}$ term that couples the coma of the lens to the astigmatism correction of the wearer is to alter the size of the reading zone. In this case the perceived reading zone would be somewhat smaller than intended by the design.

Figure 5:
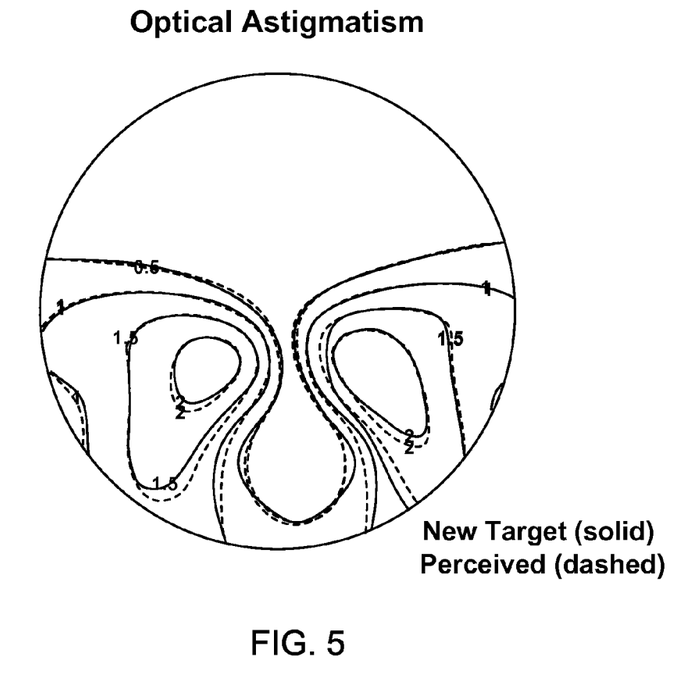
FIG. 5 is a contour plot showing a compensated astigmatism distribution for a PAL and the resulting astigmatism distribution perceived by the wearer.

In order to compensate for this loss of reading area, the cylinder value of the Rx is modified by an amount equal in magnitude and opposite in sign. FIG. 5 shows the effect of such modification. The wider reading zone of the new correction brings the effective reading zone for this wearer back to that of the original design.

Figure 6A:
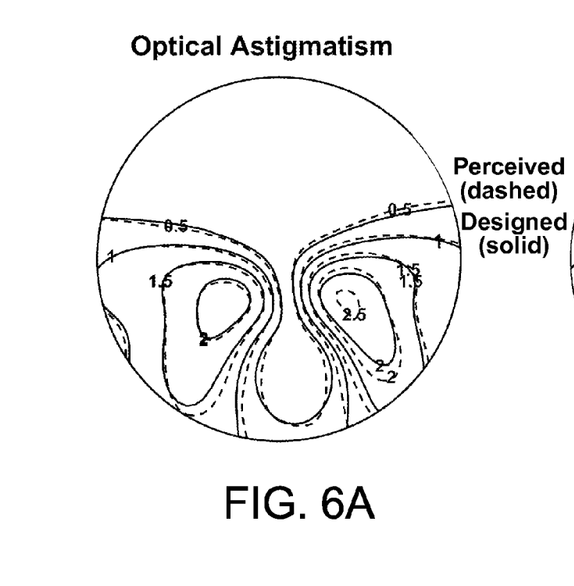
Figure 6B:
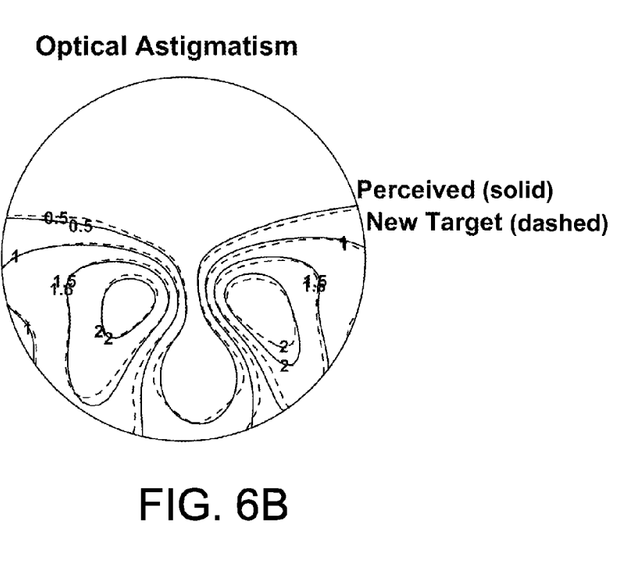

Referring to FIGS. 6A and 6B, consider a further example where an additional non-zero individual HOA coefficient in addition to the example discussed previously. Here a coefficient,)$\beta_3^{-3}=5$, the one that couples the trefoil of the lens to the other cylinder component of the correction; $J_{45}$, is considered. In addition to the change in size of the near zone the wearer would also perceive a rotation of the distance zone boundary, as seen in the plot in FIG. 6A.

Pre-compensating the target in this case has the affect of rotating the distance zone in the opposite direction, as well as widening the near zone, so that again the wearer's perceived astigmatism distribution is restored to that of the original design, as is evident from the plot in FIG. 6B.

In general, all coupling coefficients, $\alpha_3^f$, $\beta_3^f$, and $\gamma_3^f$ (f=-3, -1, 1, 3) may be non-zero. The presence of these non-zero coupling coefficients may cause complicated variations in both the astigmatism distribution and the mean power distribution. The main variables in this approach are how many HOAs to consider in the alteration of the target distribution, and how many coupling ("Taylor series") coefficients to calculate and apply to the various HOAs of the lens. In some embodiments, a linear Taylor series correction term for coma in the lens is included. In some embodiments, terms higher than third order terms (e.g., fourth order terms, fifth order terms) may have to be included. In general, the inclusion of higher order HOAs of the lens, and higher power Taylor series terms may be beneficial.

Furthermore, there are many ways to modifying the design distribution other than scaling the HOAs of the lens by coupling (Taylor) coefficients derived from the HOAs of the eye. The Taylor series approach may be the most efficient and may yield the greatest benefit from using the fewest coefficients/fewest computations to achieve a satisfactory correction of the design distribution.

In general, the methods described in this specification can be implemented, partially or entirely, in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on a computer storage medium for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

Other embodiments are in the claims.

What is claimed is:

1. A method for designing a progressive lens, the method comprising:
    obtaining a wavefront measurement of an eye, the wavefront measurement comprising information about second order aberrations of the eye and about higher order aberrations of the eye;
    determining an initial design for the progressive lens based on the wavefront measurement, the initial design comprising, for one or more points on the lens, information about second order aberrations of the progressive lens and higher order aberrations of the progressive lens, the initial design providing a target correction for the eye in the absence of the higher order aberrations of the eye;
    determining information about how changes in one or more higher order aberrations of the eye affect a second order correction for the aberrations of the eye based on information derived from the wavefront measurement;

modifying the initial design of the progressive lens using a computer processor to provide a final progressive lens design, wherein the modification accounts for an expected variation of the correction from the target correction due to one or more higher order aberrations of the initial progressive lens design and the information about how changes in one or more higher order aberrations of the eye affect the second order correction for the aberrations of the eye; and outputting the final lens design.

2. The method of claim 1, wherein the initial design of the progressive lens is based on the second order correction for the aberrations of the eye determined from the wavefront measurement.

3. The method of claim 2, wherein the initial design is a stock progressive lens design corresponding to the second order correction for the aberrations of the eye.

4. The method of claim 1, wherein determining information about how changes in one or more higher order aberrations of the eye affect the second order correction for the aberrations of the eye comprises determining a power series expansion of the aberrations of the eye.

5. The method of claim 4, wherein the power series expansion is a Taylor series expansion.

6. The method of claim 4, wherein the power series expansion comprises a linear term for at least one third order aberration of the eye.

7. The method of claim 4, wherein the power series expansion comprises a linear term for coma.

8. The method of claim 1, wherein determining information about how one or more higher order aberrations of the eye affect the second order correction for the aberrations of the eye comprises determining a scalar quantity coupling each of the one or more of the higher order aberrations of the eye to each of the second order corrections.

9. The method of claim 1, wherein the higher order aberrations of the eye comprise third order aberrations.

10. The method of claim 9, wherein the higher order aberrations of the eye further comprise fourth order aberrations.

11. The method of claim 1, wherein modifying the initial design of the progressive lens to provide a final progressive lens design comprises finding a vergence of the initial design, modifying that vergence into a new target vergence, and optimizing a lens design to correspond to the new target vergence, the optimized lens design being the final progressive lens design.

12. The method of claim 1, wherein modifying the initial design of the progressive lens to provide a final progressive lens design comprises compensating second order correction values at multiple locations on the initial design based on the one or more higher order aberrations of the initial progressive lens design at each location and the information about how changes in one or more higher order aberrations of the eye affect the second order correction for the aberrations of the eye.

13. The method of claim 12, wherein modifying the initial lens design further comprises optimizing a lens design having the compensated second order correction values.

14. The method of claim 13, wherein the optimizing is performed using a cost function.

15. The method of claim 14, wherein the optimizing is performed by determining a least squares sum of the cost function.

16. The method of claim 1, wherein obtaining the wavefront measurement comprises making a measurement of the eye using a wavefront measurement device.

17. The method of claim 1, further comprising making a progressive lens element based on the final progressive lens design.

18. A progressive lens element produced according to a final progressive lens design determined using the method of claim 1.

19. A non-transitory computer readable storage medium encoded with executable instructions comprising:
instructions operable on a processor to determine an initial design for the progressive lens based on a wavefront measurement of the eye, the initial design comprising, for one or more points on the lens, information about second order aberrations of the progressive lens and higher order aberrations of the progressive lens, the initial design providing a target correction for the eye in the absence of higher order aberrations of the eye;
instructions operable on a processor to determine information about how one or more higher order aberrations of the eye affect a second order correction for the aberrations of the eye based on information derived from a wavefront measurement of the eye;
instructions operable on a processor to modify the initial design of the progressive lens to provide a final progressive lens design, wherein the modification accounts for an expected variation of the correction from the target correction due to one or more higher order aberrations of the initial progressive lens design and the information about how one or more higher order aberrations of the eye affect the second order correction for the aberrations of the eye; and
instructions operable on a processor to output the final progressive lens design.

20. A system for determining a progressive lens design for a patient's eye, the system comprising:
a processor, and
the non-transitory computer readable storage medium encoded with executable instructions of claim 19,
wherein during operation the processor executes the instructions stored on the storage medium and the system outputs the final progressive lens design.

21. A method for designing a progressive lens, the method comprising:
determining an initial design for the progressive lens based on a prescription for an eye, the initial design providing a target correction for the eye in the absence of third or higher order aberrations of the eye;
determining how the prescription for the eye changes due to contributions from third or higher order aberrations of the eye;
determining information about one or more third or higher order aberrations of the lens for multiple locations on the initial lens design;
modifying, using a computer processor, the initial design of the progressive lens to provide a final progressive lens design, wherein the modification comprises compensating the initial lens design at the multiple locations to account for an expected variation of the correction for the eye from the target correction due to the one or more third or higher order aberrations of the initial progressive lens design and how the prescription for the eye changes due to contributions from third or higher order aberrations of the eye; and
outputting the final lens design.

22. A non-transitory computer readable storage medium encoded with executable instructions comprising:
instructions operable on a processor to determine an initial design for the progressive lens based on a prescription for an eye, the initial design providing a target correction for the eye in the absence of third or higher order aberrations of the eye;

instructions operable on a processor to determine how the prescription for the eye changes due to contributions from third or higher order aberrations of the eye;

instructions operable on a processor to determine information about one or more third or higher order aberrations of the lens for multiple locations on the initial lens design;

instructions operable on a processor to modify the initial design of the progressive lens to provide a final progressive lens design, wherein the modification comprises compensating the initial lens design at the multiple locations to account for an expected variation of the correction for the eye from the target correction due to the one or more third or higher order aberrations of the initial progressive lens design and how the prescription for the eye changes due to contributions from third or higher order aberrations of the eye; and instructions operable on a processor to output the final lens design.

23. A system for determining a progressive lens design for a patient's eye, the system comprising:

a processor, and the non-transitory computer readable storage medium encoded with executable instructions of claim 22, wherein during operation the processor executes the instructions stored on the storage medium and the system outputs the final progressive lens design.

24. The non-transitory computer readable storage medium of claim 19, wherein the instructions operable on the processor to determine information about how one or more higher order aberrations of the eye affect a second order correction for the aberrations of the eye comprises determining a scalar quantity coupling each of the one or more of the higher order aberrations of the eye to each of the second order corrections.

25. The method of claim 21, wherein determining how the prescription for the eye changes due to contributions from third or higher order aberrations of the eye comprises determining a scalar quantity coupling the one or more of the higher order aberrations of the eye to a second order correction in the prescription.

26. The method of claim 21, wherein determining how the prescription for the eye changes due to contributions from third or higher order aberrations of the eye comprises determining information about how changes in one or more higher order aberrations of the eye affect a second order correction for the aberrations of the eye in the prescription based on information derived from a wavefront measurement.

27. The non-transitory computer readable storage medium of claim 22, wherein the instructions operable on the processor to determine how the prescription for the eye changes due to contributions from third or higher order aberrations of the eye comprise instructions for determining a scalar quantity coupling one of the third or higher order aberrations of the eye to a second order correction in the prescription.

28. The non-transitory computer readable storage medium of claim 22, wherein the instructions operable on the processor to determine how the prescription for the eye changes due to contributions from third or higher order aberrations of the eye comprise instructions to determine information about how changes in one or more third or higher order aberrations of the eye affect a second order correction for the aberrations of the eye in the prescription based on information derived from a wavefront measurement.

* * * * *

UNITED STATES PATENT AND TRADEMARK OFFICE
CERTIFICATE OF CORRECTION

PATENT NO.        : 8,985,767 B2
APPLICATION NO.   : 13/722892
DATED             : March 24, 2015
INVENTOR(S)       : Ray Steven Spratt, Darryl Meister and Timo Kratzer It is certified that error appears in the above-identified patent and that said Letters Patent is hereby corrected as shown below:

In the Specification

Col. 1, line 16, delete "opthalmic" and insert --ophthalmic--.

Col. 1, line 26, delete "opthalmic" and insert --ophthalmic--.

Col. 3, line 2, delete "Chebychev" and insert --Chebyshev--.

Col. 5, line 42, delete "PAL" and insert --PAL;--.

Col. 8, line 22, delete "negligile)." and insert --negligible).--.

Col. 8, line 31, should read -- $\beta_3^{-3} \approx \left(J_{45}(Z_3^{-3} = eye + \varepsilon) - J_{45}(Z_3^{-3} = eye)\right)/\varepsilon$, etc. and --.

Signed and Sealed this
Fifteenth Day of September, 2015

Michelle K. Lee
*Director of the United States Patent and Trademark Office*